(12) United States Patent
Goldberg et al.

(10) Patent No.: US 7,238,849 B2
(45) Date of Patent: Jul. 3, 2007

(54) ADHESIVE DISPENSING ARRANGEMENT

(75) Inventors: Barbara Sheila Goldberg, Apartment 18, 17 John St., New York, NY (US) 10038; Patricia Ann Crossley, Apartment 28, 33 Ossiers Road, London (GB) SW18 1NL; Johan Christiaan Fitter, Apeldoorn (NL); Brian Lester Wolfowitz, Sandton (ZA)

(73) Assignees: Barbara Sheila Goldberg, Sandton (ZA); Patricia Ann Crossley, Bryanston (ZA)

( * ) Notice: Subject to any disclaimer, the term of this patent is extended or adjusted under 35 U.S.C. 154(b) by 2 days.

(21) Appl. No.: 10/923,866

(22) Filed: Aug. 24, 2004

(65) Prior Publication Data
US 2005/0027229 A1 Feb. 3, 2005

Related U.S. Application Data

(63) Continuation of application No. 09/936,608, filed as application No. PCT/IB00/00217 on Mar. 1, 2000, now abandoned.

(30) Foreign Application Priority Data

Mar. 17, 1999 (ZA) .................................... 99/2144

(51) Int. Cl.
*A61F 13/00* (2006.01)
(52) U.S. Cl. ...................... 602/48; 604/307; 424/448; 602/57; 602/58

(58) Field of Classification Search ............ 602/41–59; 424/443–449; 128/888, 889; 604/304–308
See application file for complete search history.

(56) References Cited

U.S. PATENT DOCUMENTS 4,192,299 A * 3/1980 Sabatano ..................... 604/305

FOREIGN PATENT DOCUMENTS

EP 0734722 A1 * 10/1996

* cited by examiner

*Primary Examiner*—Kim M. Lewis
(74) *Attorney, Agent, or Firm*—William J. Sapone; Coleman Sudot Sapone P.C.

(57) ABSTRACT

An adhesive dispensing arrangement (10) comprises an adhesive patch (12), a sachet (14), a sachet sealing strip (16), a pair of parallel gauze flaps (18A and 18B), and a peelable backing strip (20). The sachet houses a medicament such as an antiseptic or anti-microbial ointment (30), and the exposable surface (32) of the sachet is formed with a series of regularly spaced apertures (34) through which the ointment (30) may be dispensed. The peeling backing strip (20) and sachet sealing strip (16) are simultaneously peeled away, thereby exposing the apertures (34), with a central portion of the sealing strip being pulled through the gap between the gauze flaps (18A and 18B). The adhesive patch (12) is then applied around the affected area, with the ointment (30) and the sachet being dispensed via the apertures onto the gauze flaps and into treating contact with the wound.

13 Claims, 2 Drawing Sheets

ADHESIVE DISPENSING ARRANGEMENT

BACKGROUND OF THE INVENTION

This invention relates to an adhesive dispensing arrangement for dispensing a substance over a particular area for treatment thereof.

Minor wounds and the like are advantageously treated with some form of antiseptic or anti-microbial ointment prior to being covered with a sticking plaster. The ointment is applied from a separate tube or dispenser either directly onto the affected skin area or onto the gauze of the plaster. This process is relatively time consuming, involving removal of the backing strip to reveal the gauze, removal of the cap on the tube of ointment, the application of ointment to the gauze and the subsequent application of the plaster to the skin surrounding the affected area. The treatment is also costly, in that an entire tube of ointment is purchased, only to be used once or twice before the remaining contents of the tube are typically discarded or reach an expiry date.

In addition, often the optimum dosage of ointment is not applied. Over-application generally results in the plaster not sticking properly, and under-application results in the wound not being treated adequately.

SUMMARY OF THE INVENTION

According to the invention there is provided an adhesive dispensing arrangement comprising an adhesive patch for covering an area to be treated, and provided with an adhesive surface for allowing the patch to stick to the area, a peelable backing covering the adhesive surface, a dispensing container sandwiched between the adhesive surface and peelable backing, and housing a substance to be dispensed over the area to be treated, an applicator arranged to facilitate the application of the substance over the area to be treated, and a release agent, the dispensing container being positioned to co-operate with the release agent which is arranged to cause the container to open or rupture on removal of the backing for releasing the substance and allowing it to be dispensed over the area to be treated via the applicator means.

In a preferred form of the invention, the applicator is maintained apart from the substance within the dispensing container and is arranged to be impregnated with the substance only after the container has ruptured, the applicator being interposed between the container and the peelable backing.

Preferably, the applicator means includes at least one absorbent pad secured to the patch along at least one marginal adhering zone, with a non-adhering zone of the pad being interposed between the dispensing container and the backing means for receiving the substance to be dispensed from the container after it has ruptured.

Conveniently, the release agent is adhesively secured to the peelable backing means, whereby the release agent is arranged to be simultaneously peeled away with the backing means to rupture or broach the container.

Advantageously, the dispensing container has at least one aperture or rupturable zone defined in the container, and the release agent is a removable sealing strip for sealing off the aperture, the sealing strip being arranged to expose the aperture on removal thereof.

Typically, the sealing strip extends between the container and the non-adhering zones of the pad, whereby the pad is arranged temporarily to splay outwardly to allow the sealing strip to exit as it is peeled away from the container.

In one form of the invention, a pair of absorbent pads are provided in the form of adjacent flaps, each flap being formed with outer marginal adhering zones which are secured to the patch and a pair of intermediate non-adhering zones which are interposed between the dispensing container and the peelable backing, with the container being secured to the patch along an intermediate adhering zone located between the outer marginal adhering zones of the flaps.

In an alternative form of the invention, the applicator is housed within the dispensing container and is impregnated with the substance with which it is stored.

The release agent may comprise a rupturing aid for broaching or removing a rupturable zone on the container so as to provide an opening in the container.

In one form of the invention, the dispensing container comprises a rupturable sachet, the rupturing zone comprises a line of weakness arranged to facilitate the tearing away of a topmost wall of the sachet, and the rupturing aid is constituted by the extent to which bonding between the top wall of the sachet and a sealing or cover strip exceeds the line of weakness bonding.

Advantageously, the adhesive patch and the peelable backing define an outer sealed container within which the dispensing container is housed.

Typically, the adhesive dispensing arrangement is in the form of a sticking plaster or adhesive bandage arrangement in a medical application, with the substance including any form of medicament.

In an alternative form of the invention, the substance is arranged to treat selected areas, and is chosen from the group including dyestuffs, etchants, chemical treatments, pigments and catalysts.

DESCRIPTION OF EMBODIMENTS

Figure 1:
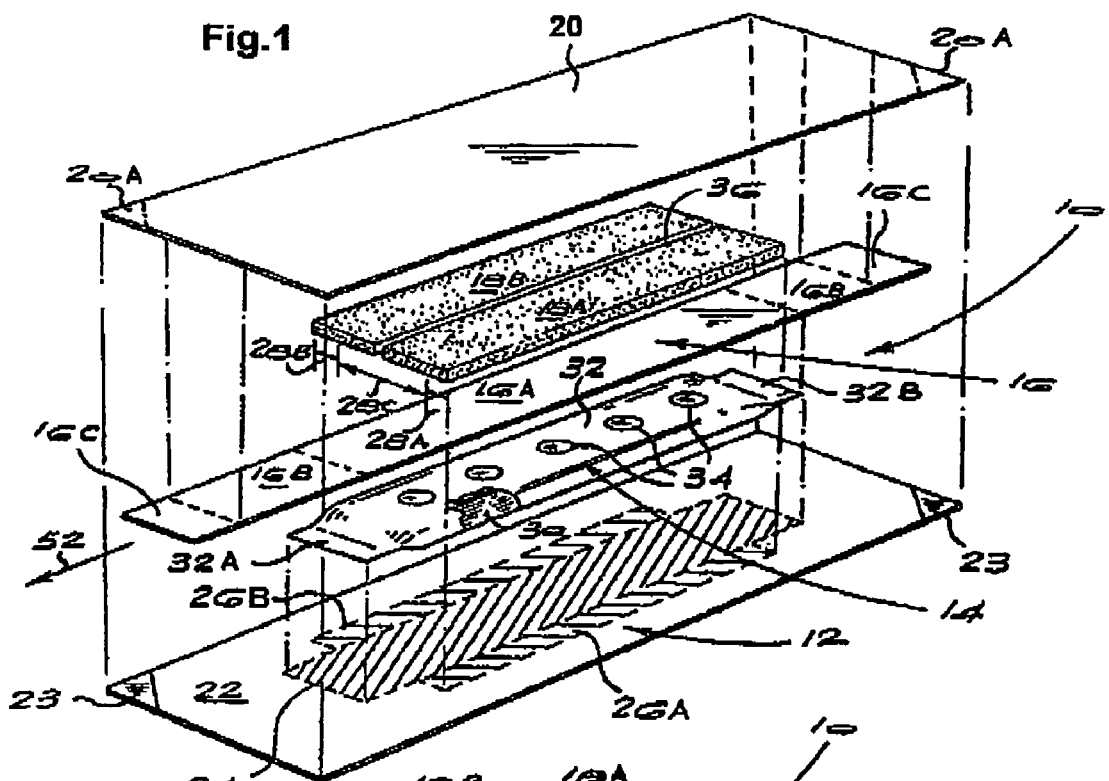
FIG. 1 shows an exploded perspective view of a first embodiment of an adhesive dispensing arrangement of the invention.
Figure 2:
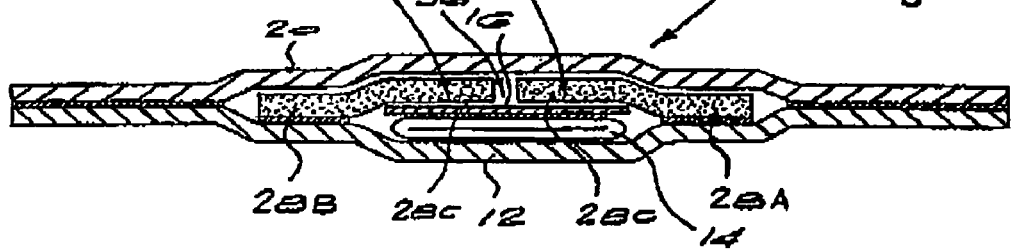
FIG. 2 shows a partly schematic cross-sectional assembled side view of the adhesive dispensing arrangement of FIG. 1.

The adhesive dispensing arrangement 10 illustrated In FIGS. 1 and 2 has as its main components a flexible cover strip or patch 12, a sachet 14 as the dispensing container, a sachet sealing strip 16, a pair of parallel gauze flaps 18A and 18B, and a peelable backing strip 20. The cover strip 12 has an inner adhesive surface 22 which is uniformly tacky, apart from non-tacky corner zones defining finger-grippable tags 23. The sachet 14 is adhesively mounted to a central rectangular zone or footprint 24 of the tacky surface 22.

Marginal rectangular zones 26A and 26B extend on either side of the central zone 24, and provide adhesive purchase for corresponding outer marginal zones 28A and 28B of the respective gauze flaps 18A and 18B. The inner marginal zones 28C of the gauze flaps do not adhere to the adhesive surface 22, but rather overlie the sachet and its sealing strip, as is clearly shown in FIG. 2.

The sachet 14 is filled with the suitable material to be dispensed, such as an antiseptic or anti-microbial ointment 30. Opposite minor ends 32A and 32B of the sachet are heat sealed, and the exposable surface 32 of the sachet is formed with a series of regularly spaced apertures 34 through which the ointment 30 may be dispensed. The sachet sealing strip 16 acts as the release means and is formed with a central sachet sealing segment 16A, the underside of which is tacky for releasably sealing off the apertures 34 to provide a protective sealed environment for the ointment 30. The sachet sealing strip is also provided with Intermediate bridging segments 16B which together correspond to the difference in length between the sachet 14 and the cover strip 12. Outer tag segments 16C protrude beyond the side edges of the cover strip 12.

Figure 4:
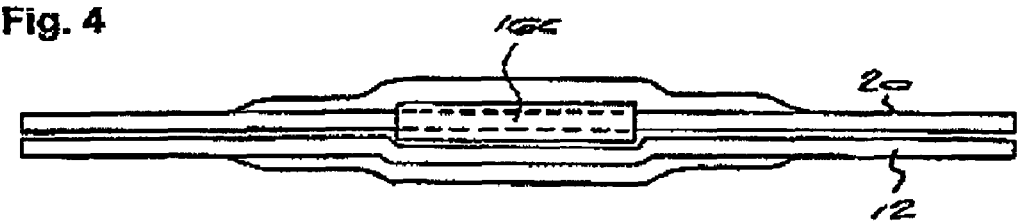
FIG. 4 shows an end-on view of another configuration of the adhesive dispensing arrangement of FIG. 1.

The top side of the central sealing segment 16A, on which the inner marginal zones 28C of the flaps rest, is non-adhering. The entire underside of the peelable backing strip 20 is mildly adhering, to the extent that a continuous outer peripheral seal is provided between the cover strip 12 and the peelable backing strip 20, so that the intermediate sachet 14, sachet sealing strip 16 and gauze strips 18A and 18B are protected against the ingress of dirt and other contaminants, as well as the possible ingress of moisture. Likewise, the outer peripheral seal prevents the egress of the aforementioned sandwiched components or their constituents. The undersides of the intermediate segments 16B adhere mildly to the adhesive surface 22, whilst the top sides of the intermediate and/or outer segments 16B and 16C are arranged to adhere relatively strongly to the peelable backing strip 20. To this end, the outer segments 16C may be folded over to the top side of the peelable backing strip in the manner illustrated In FIG. 4 to obtain additional purchase. In summary, the combined adhesion of the sachet sealing strip 16 to the peelable backing strip is greater than the combined adhesion of the sealing strip 16 both to the cover strip 12 and to the exposable surface 32 of the sachet.

The dispensing plaster is used in the following manner. The peelable backing strip is first removed by gripping adjacent non-adhering corner tags 23 and 20A and pulling them apart from one another. The sachet sealing strip 16 is carried with the backing strip as it is peeled away by virtue of the aforementioned stronger bond that it has with the backing strip 20. The apertures 34 are successively exposed as the sachet sealing strip 16 is removed, with the central portion of segment 16A of the sealing strip being pulled through the ever-widening gap 36 between the gauze flaps 18A and 18B as their central non-adhering portions lift and separate. The gauze flaps 18A and 18B revert to a substantially flattened condition after removal of the backing strip 20 and the accompanying sachet sealing strip 16 to at least partly cover the exposed sachet apertures 34.

Figure 2A:
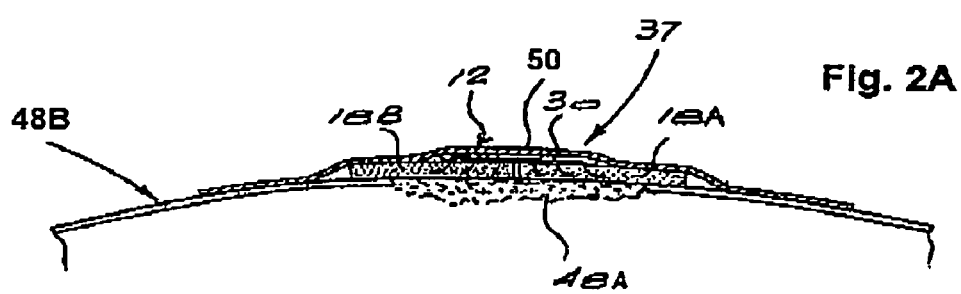
FIG. 2A shows a partly schematic cross-sectional side view of the dispensing arrangement of FIG. 2 in position on an area to be treated.

The remaining assembly comprising the cover strip, the newly vented or ruptured surface 32 and the gauze flaps 18A and 18S which act as applicator means are now ready for application. At this stage, an initial release of ointment 30 or the like into the overlying gauze flaps 18A and 18B may commence. As is shown in FIG. 2A, the assembly 37, which essentially resembles a modified gauze sticking plaster, is applied to the affected area, with the gauze flaps 18A and 18B covering the wound or affected area 48A and the tacky surface 22 of the cover strip adhering to the surrounding skin 48B. Slight finger pressure on the exposed surface 50 of the cover strip 12 will cause further dispensing of the ointment 30 in the sachet through the apertures 34 for infusion into the applicator means, which are the gauze flaps 18A and 18B and ultimate treating contact with the wound. Even spacing of the apertures 34 ensures an evenly spread infusion of the ointment into the gauze flaps 18A and 18B.

In medical applications, the substance to be dispensed is not limited to an ointment, but may be more free-flowing and liquid in form. Typical medical preparations may include anti-microbial, antibacterial, antiviral and antiseptic agents, as well as antibiotics and anti-fungal agents. The substances may also include corticosteroids either singularly or with anti-infective agents, local anaesthetic agents and anti-psoriatic preparations. Salicylic acid, silicone gel, and anti-inflammatory agents may also be incorporated. The contents of the sachet may also include vitamin derivatives, hormones, hair growth stimulants, emolients and protectives, as well as antihistamines and anti-metabolites. In a particular embodiment, the substance to be dispensed includes Bactroban®, a topical ointment made by Smith-Kline Beecham, a preparation of 2 grams of mupirocin in 100 grams of a water soluble base.

In the case of non-medical general purpose application, the cover strip may be of a more robust construction, and the substance to be dispensed may include, inter alia, a chemical, a dye, a pigment or a catalyst. If the substance to be dispensed has aggressive properties, or is extremely fluid, the sealing strip 16 may be omitted from the assembly, and suitable rupturing zones may be formed in place of the apertures 34. These rupturing zones remain intact under conditions of normal storage and handling, but are then encouraged to rupture subsequent to placement of the cover strip onto the surface to be treated. Rupturing of the sachet may be induced by additional pressure on the outer surface 50 of the cover strip after it has been stuck onto the area. The sachet sealing strip 16 may be replaced by other release means such as an appropriate length of cord or other rupture-inducing means extending into and anchored within the sachet for at least initiating rupturing of the sachet along a weakened zone.

In one form of the invention, the sealing strip 16 or other contents release means may be made to operate independently of the peelable backing strip 20. For example, the cover strip may be positioned over the area to be treated with the sachet intact, after which the sealing strip or the like is removed so as to rupture the sachet and begin the dispensing process.

It will be appreciated that the shape and orientation of the various components described above is almost unlimited, and that a single gauze flap may be used in place of a pair of flaps. In a still further modification, a single gauze pad bridges the sachet transversely, and is adhesively anchored to both of the marginal zones 26A with the sachet sealing strip 16 being removed by pulling it along its axis in the direction of arrow 52. In this case, the strip may be at least twice as long as the sachet, and folded double, with the upper free end of the strip being gripped to promote a peeling effect.

In a still further variation, the gauze and the sachet may contain different substances, which, when mixed on rupturing to the sachet, react to cause the desired effect on the surface to be treated. More than one sachet, or a multi-compartment sachet may also be used, each rupturable compartment containing miscible substances.

Figure 3:
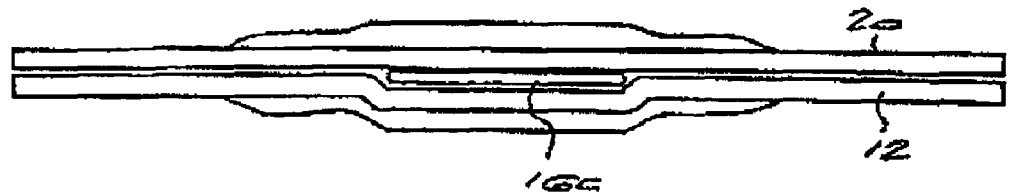
FIG. 3 shows an end-on view of one configuration of the dispensing arrangement of FIG. 1.

In FIG. 3, an end-on view of the end face of an assembled adhesive dispensing arrangement 10 clearly illustrates the protruding outer segment 16C of the sachet sealing strip 16. In this version, the peelable backing strip 20 may be removed independently of the sealing strip 16, as opposed to the previously described FIG. 4 version. The backing strip may in this case be a double length folded over strip of the type described above.

Figure 5:
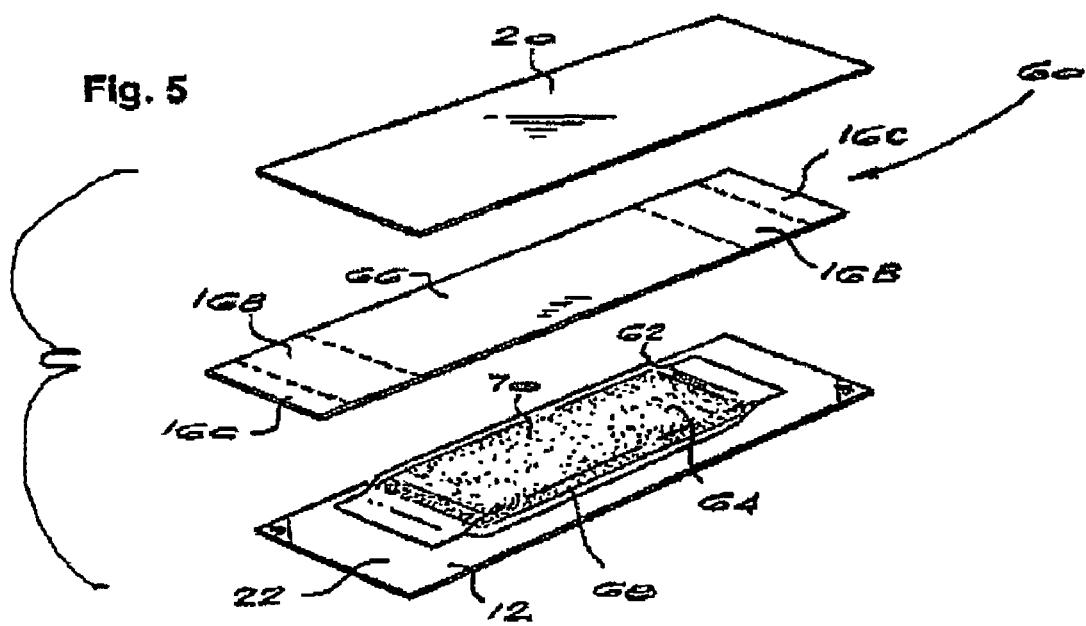
FIG. 5 shows an exploded perspective view of a second embodiment of an adhesive dispensing arrangement of the invention.

Referring now to FIG. 5, a second embodiment of an adhesive dispensing arrangement 60 is shown which differs primarily from the first embodiment in that the gauze flaps 18A and 18B of FIG. 1 are incorporated into a dispensing container, sachet 62 as a single gauze pad 64. The gauze pad 64 is typically impregnated with the substance to be dispensed, as is the case with paraffin gauze. Both the underside and the top sides of the sachet 62 are adhesively attached to the respective adhesive face 22 of the cover strip 12 and a lower adhesive face of a sachet sealing strip 66. A parting line or zone of weakness 68 runs around a low perimeteral side wall of the sachet 62. The peelable backing strip 20 and the sachet sealing strip 66 co-operate in the same manner as was described with reference to FIG. 1. As the backing and cover strips 20 and 22 are peeled away from one another, the bond between the sealing strip 66 and the upper surface of the sachet 62 is sufficient to result in the topmost wall 70 of the sachet being torn away along the parting line 68 so as to expose the impregnated gauze pad 64. The exposed gauze pad 64 and cover strip 12 are then applied to the area to be treated in the manner of a conventional sticking plaster subsequent to the removal of its backing strip.

Figure 6:
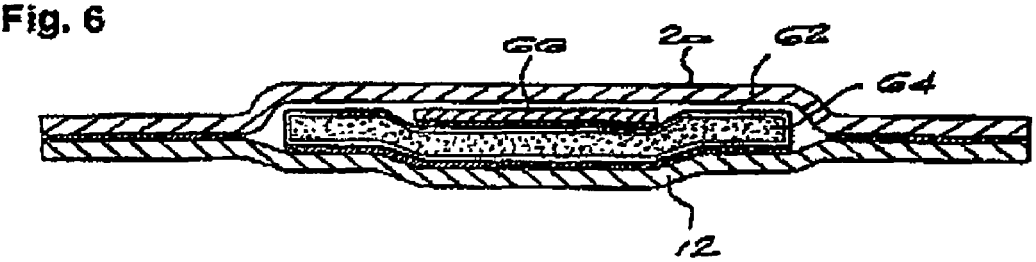
FIG. 6 shows a partly schematic cross-sectional assembled side view of the adhesive dispensing arrangement of FIG. 5.

The assembled dispensing arrangement 60 is shown in FIG. 6. It will be appreciated that both the gaps and the material thicknesses in FIGS. 2 and 6 are not illustrative, but merely serve to indicate more clearly the different components making up the arrangements. In both FIGS. 2 and 6, the hatched line interfaces are indicative of adhesive bonds existing at the interfaces.

The impregnated gauze pad allows for more even and immediate distribution of the ointment or the like over the wound area. Such immediate distribution could result in the soaked gauze pad inadvertently contacting the skin surrounding the wound or treatment area.

In a still further embodiment of the invention, the sachet sealing strip 66 may be removed completely, with the top wall 70 of the sachet adhering to the underside of the peelable backing strip 20. As was the case with the sealing strip, the adhesion between the backing strip and the top wall 70 of the sachet would be sufficient to cause the top wall of the sachet to tear away completely along the parting line 68 so as to expose the impregnated gauze 64.

Typically, the sachet is manufactured and filled during a separate manufacturing operation, after which it is incorporated with the other components of the dispensing arrangement. A number of advantages are attached to the provision of a separate sachet. Such sachets may be filled with specialized medicaments which are customarily not produced by plaster/adhesive bandage manufacturers. The sachets may then be transported to a specialist plaster or adhesive bandage manufacturer. In addition, where non-uniform conditions of sterility exist, in that the sachets need to be manufactured and filled under more stringent conditions than the manufacture of the adhesive bandages, different production fines having different sterility requirements.

In a still further embodiment, the top wall 70 of the sachet may effectively be constituted by the backing strip itself with the gauze pad 64 being anchored directly onto the cover strip 12. In this even simpler version, the cover strip 12 and peelable backing strip 20 in combination effectively provide the sachet within which the gauze pad 64 is sealed. A more rigorous and continuous outer peripheral seal is provided between the cover strip 12 and the backing strip 20 for securely containing the gauze pad 64 and its contents.

A significant advantage of the present invention, and in particular the preferred embodiments in which a separate sachet is provided, is that the sachet constitutes an effective barrier to prevent cross-contamination either from or into the sachet. The substance to be dispensed may be incorporated into this sachet under sterile conditions. Further, the dispensing of the ointment occurs directly after the backing strip has been removed, thereby reducing the chances of contamination. This procedure differs considerably over typically non-sterile conditions in which ointment from a separate potentially contaminating tube is dispensed onto the gauze pad of conventional medical plasters. The outer peripheral tacky zone of the cover strip seals and surrounds the ointment, the gauze pad(s) and the wound, thereby promoting wet wound healing.

The invention claimed is:

1. An adhesive dispensing arrangement comprising:
   a patch having an inner surface for covering an area to be treated, the inner surface having an adhesive on at least a portion thereof for allowing the patch to stick to an area adjacent the area to be treated;
   a dispensing container for holding a substance to be dispensed onto the area to be treated, the dispensing container retained on a portion of the inner adhesive surface;
   applicator means for applying the substance to the area to be treated, the applicator means being disposed to at least partially overlie the dispensing container, and having at least one portion thereof mounted to the inner adhesive surface and at least one portion which is non-adhering thereto;
   a removable release means located at least partially between the dispensing container and the applicator means, the applicator means at least one non-adhering portion disposed to at least partially overlie the removable release means and being arranged to allow the removable release means to be at least partially removed from the dispensing container, thereby opening the dispensing container to permit the substance to be released therefrom; and,
   a peelable backing for covering the applicator means, and a portion of the inner adhesive surface, such that removing the peelable backing enables removal of the release means for allowing dispensing of the substance from the dispensing container to the applicator means and thereby to the area to be treated.

2. The adhesive dispensing arrangement according to claim 1 wherein the applicator means comprise at least one absorbent pad secured to the inner adhesive surface along at least one marginal adhering zone, a non-adhering zone of the pad being disposed to at least partially overlie the dispensing container.

3. The adhesive dispensing arrangement according to claim 1 wherein the release means has at least one portion engaged to the peelable backing, for co-removal therewith.

4. The adhesive dispensing arrangement according to claim 1 wherein the release means has two portions adhesively secured to the peelable backing, for co-removal therewith.

5. The adhesive dispensing arrangement according to claim 1 wherein the dispensing container has at least one aperture, the removable release means sealing the aperture, removal of the release means exposing the aperture for dispensing the substance therethrough.

6. The adhesive dispensing arrangement according to claim 1 wherein the removable release means is a sealing strip.

7. The adhesive dispensing arrangement according to claim 1 wherein the substance is a medicament.

8. The adhesive dispensing arrangement according to claim 1 wherein the substance is selected from the group consisting of dyestuffs, etchants, chemical treatments, pigments and catalysts.

9. The adhesive dispensing arrangement according to claim 1 wherein the release means is engaged to a portion of the dispensing container to remove the portion when the release means is removed to thereby release the substance therefrom.

10. The adhesive dispensing arrangement according to claim 9 wherein the release means has an adhesive for bonding the release means to the portion of the dispensing container, such that removal of the release means tears away the adhered portion of the dispensing container.

11. The adhesive dispensing arrangement according to claim 1 wherein the applicator means is a gauze pad.

12. The adhesive dispensing arrangement of claim 1 wherein the dispensing container is a sachet.

13. An adhesive dispensing arrangement comprising:
a patch having an inner surface for covering an area to be treated, the inner surface having an adhesive on at least a portion thereof for allowing the patch to stick to an area adjacent the area to be treated;

a dispensing container for holding a substance to be dispensed onto the area to be treated, the dispensing container retained on a portion of the inner adhesive surface;

applicator means for applying the substance to the area to be treated, the applicator means being disposed to at least partially overlie the dispensing container, and having at least a portion thereof mounted to the inner adhesive surface;

a removable release means located at least partially between the dispensing container and the applicator means, removal of the release means opening the dispensing container to permit the substance to be released therefrom; and, a peelable backing for covering the applicator means, and a portion of the inner adhesive surface, such that removing the peelable backing enables removal of the release means for allowing dispensing of the substance from the dispensing container to the applicator means and thereby to the area to be treated, the applicator means being a pair of absorbent pads, each pad having an outer marginal adhering zone secured to the inner adhesive surface, and each pad having a non-adhering zone disposed to at least partially overlie the removable release means, the non-adhering zones being movable to allow the removable release means to be peeled away from the dispensing container.

* * * * *

UNITED STATES PATENT AND TRADEMARK OFFICE
CERTIFICATE OF CORRECTION

PATENT NO. : 7,238,849 B2  Page 1 of 1
APPLICATION NO. : 10/923866
DATED : July 3, 2007
INVENTOR(S) : Barbara Sheila Goldberg et al.

It is certified that error appears in the above-identified patent and that said Letters Patent is hereby corrected as shown below:

On the title page, item [73]; should read:
ASSIGNEES: Barbara Sheila Goldberg, New York NY; Patricia Ann Crossley, London, GB Signed and Sealed this Eighteenth Day of September, 2007

JON W. DUDAS
*Director of the United States Patent and Trademark Office*